US007990251B1

(12) United States Patent
Ford, Jr.

(10) Patent No.: US 7,990,251 B1
(45) Date of Patent: Aug. 2, 2011

(54) DRUG MANAGEMENT SYSTEMS

(76) Inventor: Herbert Ford, Jr., Glendale, AZ (US)

( * ) Notice: Subject to any disclaimer, the term of this patent is extended or adjusted under 35 U.S.C. 154(b) by 1097 days.

(21) Appl. No.: 11/750,270

(22) Filed: May 17, 2007

Related U.S. Application Data

(60) Provisional application No. 60/747,522, filed on May 17, 2006.

(51) Int. Cl.
G08B 5/22 (2006.01)
G09F 25/00 (2006.01)
G06F 3/048 (2006.01)

(52) U.S. Cl. ............. 340/286.07; 340/286.01; 715/764; 715/767

(58) Field of Classification Search .................. None
See application file for complete search history.

(56) References Cited

U.S. PATENT DOCUMENTS

| 4,709,331 A | 11/1987 | Barkett et al. |
| 5,609,575 A | 3/1997 | Larson et al. |
| 5,630,664 A | 5/1997 | Farrelly |
| 6,167,412 A | 12/2000 | Simons |
| 6,978,286 B2 | 12/2005 | Francis et al. |
| 2002/0130779 A1 | 9/2002 | Ford |
| 2003/0062989 A1* | 4/2003 | Tsunezumi ............... 340/286.07 |
| 2004/0230457 A1 | 11/2004 | Rosenbloom et al. |
| 2005/0224083 A1 | 10/2005 | Crass et al. |
| 2006/0047538 A1* | 3/2006 | Condurso et al. ................. 705/3 |
| 2006/0258985 A1* | 11/2006 | Russell ......................... 604/151 |
| 2007/0109325 A1* | 5/2007 | Eveleigh ....................... 345/684 |
| 2007/0116036 A1* | 5/2007 | Moore .......................... 370/462 |
| 2009/0043290 A1* | 2/2009 | Villegas et al. ............ 604/891.1 |
| 2009/0183147 A1* | 7/2009 | Davis et al. .................... 717/168 |
| 2009/0247931 A1* | 10/2009 | Damgaard-Sorensen ...... 604/19 |

FOREIGN PATENT DOCUMENTS

WO WO2004068308 A2 8/2004

* cited by examiner

*Primary Examiner* — Julie Lieu
(74) *Attorney, Agent, or Firm* — Jeffrey D. Moy; Weiss & Moy, P.C.

(57) ABSTRACT

A system to electronically assist health care professionals quickly and efficiently calculate dosages and infusion rates for emergency drugs. The system comprises a portable handheld calculator incorporating user input keys dedicated to commonly prescribed drugs, quick entry of default drug values, and toggles between at least two operational modes, specifically between adult and pediatric modes. In addition, the system alarms on the entry of "out-of-range" drug values, titrates, immediately ascertains compatibilities between drugs, and allows the updating of stored drug parameters by means of physical or wireless data ports.

20 Claims, 6 Drawing Sheets

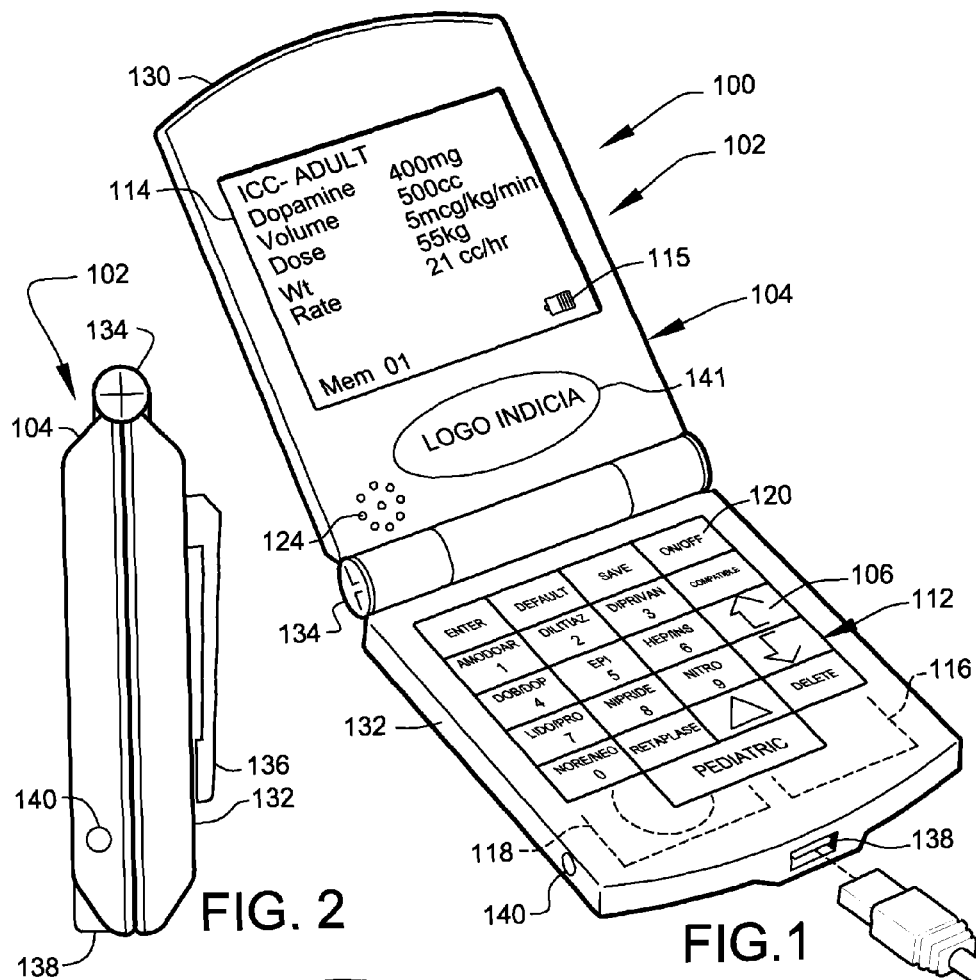
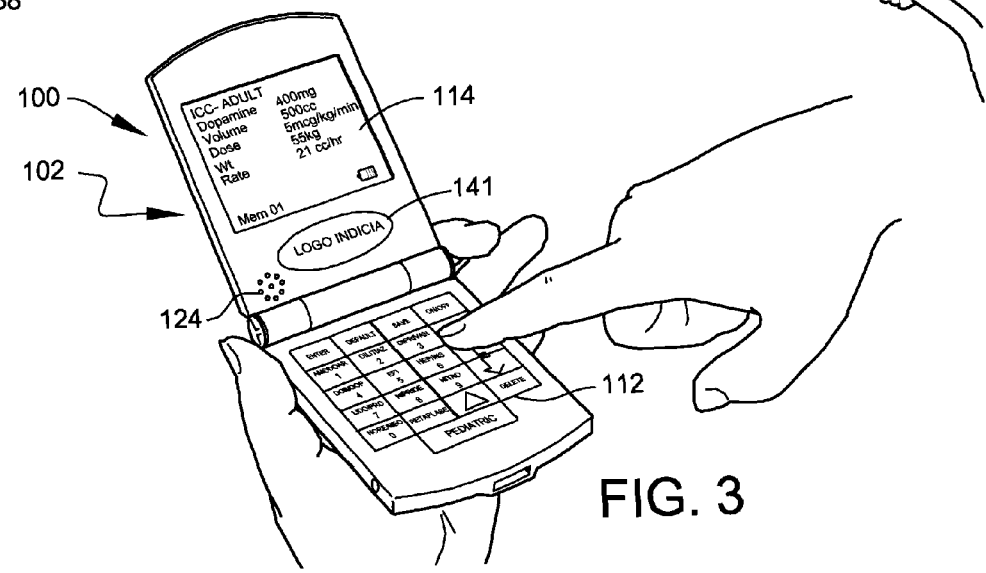

DRUG MANAGEMENT SYSTEMS

CROSS-REFERENCE TO RELATED APPLICATION

The present application is related to and claims priority from prior provisional application Ser. No. 60/747,522, filed May 17, 2006, entitled "DRUG MANAGEMENT SYSTEMS", the contents of which are incorporated herein by this reference and are not admitted to be prior art with respect to the present invention by the mention in this cross-reference section.

BACKGROUND

This invention relates to providing systems for improving medical safety in the area of intravenous drug administration. More particularly, this invention relates to hand-held electronic medical systems adapted to assist health care professionals quickly and efficiently calculate dosages and infusion rates for commonly administered drugs, especially emergency drugs. The system is also circumstantially adaptable to non-emergency drug administration procedures.

Intravenous drugs are commonly infused in critical care situations such as during a cardiopulmonary resuscitation or trauma stabilization where resuscitative drugs are administered as a life-saving measure. Such drugs may preferably include: Isoproterenol, Lidocaine Hydrochloride, Procanamide Hydrochloride, Phenylephrine Hydrochloride, Sodium Nitropusside, Dilitiazem Hydrochloride, Dobutamine Hydrochloride, Dopamine Hydrochloride, Norepincphrine, Heparin Sodium, Insulin Regular, Adrenaline, Lidocaine and Nitroglycerine. The safe and efficacious (typically intravenous at present) administration of such drugs is often dependent upon physical factors such as age and weight of the patient. Each drug infusion rate calculation is therefore generally dependent on a number of patient factors.

Conventionally, medical professionals are required to recall the formulas applicable to each category of drug, to determine the weight of the patient, and to manually calculate proper dosage (i.e., drip rate) based upon the parameters prescribed by the attending physician, the drug prescribed, volume of intravenous fluid, and other critical parameters. A particular problem which arises with manual calculations is that, quite often, a medical professional in critical care situation is operating within a dynamic and highly stressful environment where speed in infusing the patient is vital in achieving a satisfactory outcome.

An example of a common method of determining drip rates is expressed in the following equation:

$$D*BW*60 = C*R$$

The variables for this equation are defined as follows:
D=Dosage Rate (mg/ml, units/ml, ug/kg/min)
BW=Body Weight expressed in kilograms (kg)
C=Concentration of infusion expressed in mg/ml or units/ml
R=Rate of infusion expressed in milliliters per hour (ml/hr)
60=Constant (60 minutes per hour)

The representative equation includes five variables requiring that a series of calculations be performed each time a drug is prepared and used.

Medical professionals are often required to rely upon their memory to recall safe dose ranges for drugs being administered during an emergency procedure. Often, a medical professional is required to manually perform the entire sequence of the calculation, relying on the knowledge of the prescribing physician as to safe drug dose ranges. In complex cases, a medical professional may stop to reconfirm the proper administration by consulting a printed medical manual, infusion "cheat sheet", or incompatibility chart. This procedure can be excessively time consuming, especially in emergency and intensive-care environments.

Unfortunately, the urgency with which such calculations must take place can sometimes result in errors. Furthermore, multiple drugs are often administered simultaneously to a given patient. Some drugs are not compatible for infusion. The medical professional must immediately identify whether a first administered drug is compatible or incompatible with one or more other drugs to be administered. Again, medical professionals are often required to commit to memory the compatibility status of drugs, and thus less-than-perfect memory endangers the welfare of the patient.

Further compounding the above-described problems is the trend toward an increasing number of pediatric patients being treated in normally adult medical facilities. In these situations, the medical professional must quickly adjust the drug administration parameters to match the needs of the pediatric patient.

Clearly, a need exists within emergency and intensive-care environments for a system adapted to quickly and efficiently provide appropriate drug infusion rate calculations and interaction data to medical professionals, thus increasing the likelihood of a successful medical outcome. Similar issues sometimes exist in the administration of non-emergency drugs.

OBJECTS AND FEATURES OF THE INVENTION

A primary object and feature of the present invention is to overcome the above-described problems.

Another object and feature of the present invention is to provide a hand-held computer system related to electronically assisting a medical professional to accurately generate at least one drug parameter output (relating to the administration of at least one emergency or non-emergency medical drug), a resultant of a medical calculation utilizing one or more user inputs by the medical professional.

A further object and feature of the present invention is to provide such a system that comprises a direct user input of one or more emergency or non-emergency drugs.

Another object and feature of the present invention is to provide such a system comprising at least two modes for altering the parameters of the drug input and/or drug calculation.

An additional object and feature of the present invention is to provide a method related to the use-promotion and accurate administration of at least one emergency or non-emergency medical drug.

A further primary object and feature of the present invention is to provide such a hand held device that is fast and efficient. Other objects and features of this invention will become apparent with reference to the following descriptions.

SUMMARY OF THE INVENTION

In accordance with a preferred embodiment hereof, this invention provides a computer system related to electronically assisting at least one medical professional to accurately generate at least one drug parameter output, relating to the administration of at least one emergency medical drug, a resultant of at least one medical calculation utilizing at least one medical drug-administration-related input by the at least one medical professional, such system comprising: hand-holdable housing means for housing such computer system; computer storage means for storing at least one drug database comprising a plurality of known medical drug parameters; first computer interface means for assisting user input of the at least one medical drug-administration-related input; second computer interface means for displaying the at least one medical drug-administration-related drug-parameter output; computer processor means for generating the at least one medical drug-administration-related drug-parameter output; and power supply means for supplying electrical power to assist operation of such computer system; wherein such first computer interface means comprises actuator-button means for user-selecting a single one of such emergency medical drugs by a single user button actuation; and wherein such first computer interface means further comprises actuator-button mode means for selecting among at least two actuator-button modes wherein each such actuator-button mode provides actuator-button access for user-selecting among a unique set of known emergency medical drug parameters. Moreover, it provides such a computer system further comprising: alarm means for generating at least one alarm signal discernable by the at least one medical professional; wherein such computer storage means comprises computer database means for providing predetermined acceptable user input ranges for the at least one medical drug-administration-related input; wherein such computer processor means comprises activator means for activating such alarm means; and wherein such activator means activates such alarm means when the at least one medical drug-administration-related input deviates from the predetermined acceptable user input ranges for the at least one medical drug-administration-related input. Additionally, it provides such a computer system further comprising drug compatibility means for determining compatibility of at least one first such at least one emergency medical drug with at least one second such at least one emergency medical drug.

In accordance with another preferred embodiment hereof, this invention provides a computer system related to electronically assisting at least one medical professional to accurately generate at least one drug parameter output, relating to the administration of at least one emergency medical drug, a resultant of at least one medical calculation utilizing at least one medical drug-administration-related input by the at least one medical professional, such system comprising: at least one hand-holdable housing adapted to house such computer system; at least one computer storage adapted to store at least one drug database comprising a plurality of known medical drug parameters; at least one first computer interface adapted to assist user input of the at least one medical drug-administration-related input; at least one second computer interface adapted to display the at least one medical drug-administration-related drug-parameter output; and at least one computer processor adapted to generate the at least one medical drug-administration-related drug-parameter output; and at least one power supply adapted to supply electrical power to assist operation of such computer system; wherein such at least one first computer interface comprises at least one actuator-button adapted to user-select a single one of such emergency medical drugs by a single user button actuation; and wherein such at least one first computer interface further comprises at least one actuator-button mode selector adapted to select among at least two actuator-button modes wherein each such actuator-button mode provides actuator-button access for user-selecting among a unique set of known medical drug parameters.

Also, it provides such a computer system further comprising: at least one alarm adapted to generate at least one alarm signal discernable by the at least one medical professional; wherein such at least one computer storage comprises at least one computer database adapted to provide predetermined acceptable user input ranges for the at least one medical drug-administration-related input; wherein such at least one computer processor comprises at least one activator signal adapted to activate such at least one alarm; and wherein such at least one activator signal is adapted to activate such at least one alarm when the at least one medical drug-administration-related input deviates from the predetermined acceptable user input ranges for the at least one medical drug-administration-related input.

In addition, it provides such a computer system further comprising at least one drug compatibility determiner for computer-determining compatibility of at least one first such at least one emergency medical drug with at least one second such at least one emergency medical drug. And, it provides such a computer system wherein: such at least one hand-holdable housing comprises at least one hinge; and such at least one hinge is situate between such at least one first computer interface and such at least one second computer interface. Further, it provides such a computer system wherein such at least one actuator-button comprises at least one first indicia indicating at least one such emergency medical drug. Even further, it provides such a computer system wherein: each such at least two actuator-button modes comprise at least one set of such first indicia; and such mode changes comprise variation in such first indicia of such at least one actuator-button.

Moreover, it provides such a computer system wherein such at least one computer storage comprises at least one drug-entry storage adapted to store the at least one medical drug-administration-related input and the at least one drug parameter output. Additionally, it provides such a computer system wherein such at least one computer processor comprises at least one editor adapted to assist at least one user edit to at least one of the least one medical drug-administration-related inputs stored within such at least one drug-entry storage. Also, it provides such a computer system further comprising at least one external data transfer port adapted to assist at least one transfer of data between at least one external data source and such at least one computer storage. In addition, it provides such a computer system wherein such at least one second computer interface comprises at least one display illuminator adapted to generate illumination assisting visual user interface. And, it provides such a computer system wherein such at least one actuator-button comprises at least one button illuminator adapted to generate illumination assisting user button interface.

Further, it provides such a computer system wherein: at least one of such at least two actuator-button modes comprises at least one adult mode; and at least one of such at least two actuator-button modes comprises at least one pediatric mode. Even further, it provides such a computer system further comprising at least one automatic power reducer adapted to automatically reduce the draw of the electrical power from such at least one power supply after at least one predetermined period without such user input at such at least one first computer interface. Moreover, it provides such a computer system wherein such emergency medical drugs of such at least one actuator-button comprises at least one member selected from the group consisting essentially of: Amiodarone, Dilitiazem, Diprivan, Dobutamine, Dopamine Hydrochloride, Ephinephrine, Heparin, Insulin, Lidocaine, Procanamide, Sodium Nitropusside, Nitroglycerine, Norepinephrine, Neosynephrine, Retaplase, and Isoproterenol.

In accordance with another preferred embodiment hereof, this invention provides a method related to the use-promotion and accurate administration of at least one medical drug comprising the steps of: providing, by at least one provider, of a plurality of hand-held computer devices relating to electronically assisting a plurality of medical professionals to accurately generate drug parameter outputs, relating to the administration of medical drugs, a resultant of medical calculations utilizing medical drug-administration-related inputs by such medical professional; providing, in at least one input interface of such hand-holdable computer devices, at least one set of actuator-buttons dedicated to at least one respective set of such medical drugs selected by such provider; and assisting use-promotion of such hand-holdable computer devices by such medical professionals; wherein use of such at least one set of such medical drugs may be promoted.

Additionally, it provides such a method wherein such at least one provider comprises at least one emergency medical drug purveyor. Also, it provides such a method wherein such hand-holdable computer devices comprise actuator-buttons bearing indicia relating to such at least one set of such medical drugs. In addition, it provides such a method wherein such medical drugs comprise emergency medical drugs.

In accordance with another preferred embodiment hereof, this invention provides a computer system related to electronically assisting at least one medical professional to accurately generate at least one drug parameter output, relating to the intravenous administration of at least one medical drug, a resultant of at least one medical calculation utilizing at least one medical drug-administration-related input by the at least one medical professional, such system comprising: hand-holdable housing means for housing such computer system; computer storage means for storing at least one drug database comprising a plurality of known medical drug parameters; first computer interface means for assisting user input of the at least one medical drug-administration-related input; second computer interface means for displaying the at least one medical drug-administration-related drug-parameter output; computer processor means for generating the at least one medical drug-administration-related drug-parameter output; and power supply means for supplying electrical power to assist operation of such computer system; wherein such first computer interface means comprises actuator-button means for user-selecting a single one of such medical drugs by a single user button actuation; and wherein such first computer interface means further comprises actuator-button mode means for selecting among at least two actuator-button modes wherein each such actuator-button mode provides actuator-button access for user-selecting among a unique set of known medical drug parameters.

And, it provides such a computer system wherein such second computer interface means comprises default-display means for displaying at least one situational-default set of the at least one medical drug-administration-related drug-parameter output. Further, it provides such a computer system wherein such first computer interface means comprises at least one dedicated "default-type" key to input at least one request to display such at least one situational-default set of the at least one medical drug-administration-related drug-parameter output.

This invention also provides each and every novel feature, element, combination, step and/or method disclosed or suggested.

BRIEF DESCRIPTION OF THE DRAWINGS

FIG. 1 shows a perspective view illustrating an intensive-care calculator of a medical drug management system according to a preferred embodiment of the present invention.

FIG. 2 shows a side view of the intensive-care calculator of FIG. 1.

FIG. 3 shows a perspective view, illustrating the intensive-care calculator of FIG. 1, held in the hand of a user during operation.

Figure 4:
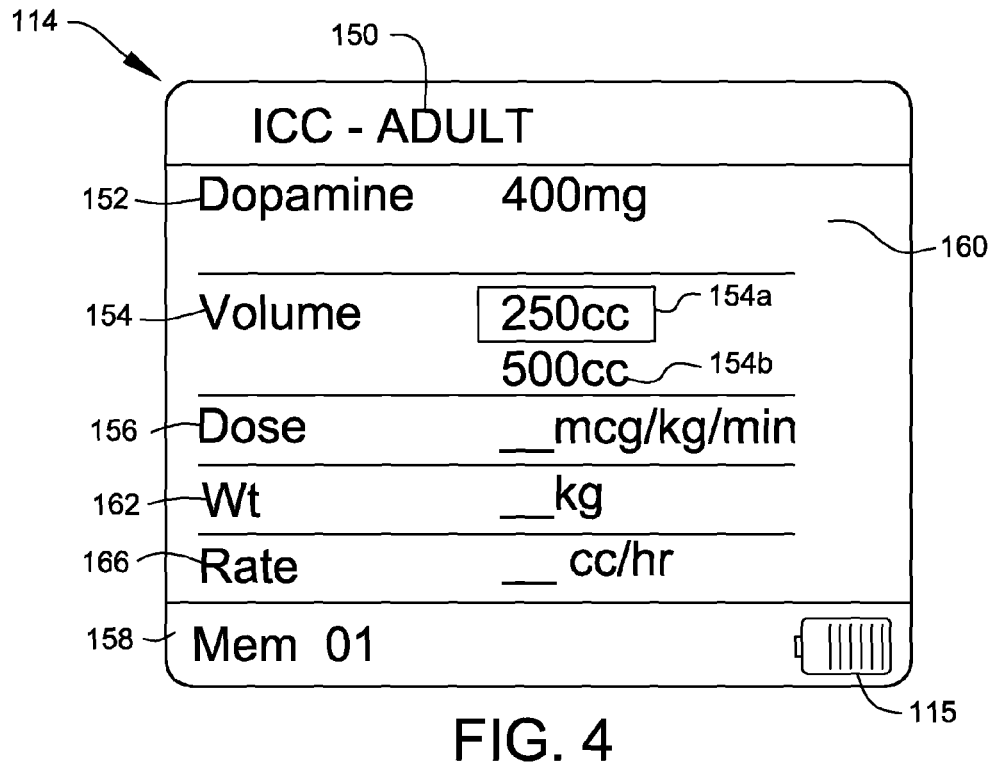
FIG. 4 shows a front view of a screen display of the intensive-care calculator, according to the preferred embodiment of FIG. 1.

DETAILED DESCRIPTION OF THE BEST MODES AND PREFERRED EMBODIMENTS OF THE INVENTION

FIG. 1 shows a perspective view illustrating intensive-care calculator 102 of medical drug management system 100 according to a preferred embodiment of the present invention. FIG. 2 shows a side view illustrating additional functions and features of intensive-care calculator 102 of FIG. 1.

Preferably, intensive-care calculator 102 electronically assists in calculating dosages and infusion rate for drugs, most preferably emergency drugs. Not only does the present invention quickly and efficiently calculate infusion rates of such drugs, but it does so in a useful and novel manner. More specifically, intensive-care calculator 102 incorporates three important supplementary features. First, intensive-care calculator 102 comprises a stored database of set parameters to assist in preventing overdosing or under dosing of drugs. Secondly, intensive-care calculator 102 allows a user to ascertain compatibilities of drugs immediately. Thirdly, intensive-care calculator 102 is preferably adapted to allow immediate changes between two or more operational modes, for example between an adult mode and a pediatric mode.

FIG. 3 shows a perspective view, illustrating intensive-care calculator 102 of FIG. 1, held in the hand of a medical professional during operation. In the present disclosure, the term "medical professional" shall be broadly defined as a person involved in a skilled medical or health related occupation, such as, for example, physicians, intensive care unit nurses, pediatric intensive care unit nurses, registered nurses, clinical nurse specialists, nurse practitioners, etc. Upon reading the teachings of this specification, those of ordinary skill in the art will now understand that, under appropriate circumstances, considering such issues as trends in categorization, changes in the healthcare profession, advances in medicine, etc., the term medical professional may include other members functioning within medical-related fields, such as, for example, medical assistants, pharmacists, medical technologists, military medics, paramedics and emergency medical technicians, medical "first responders", trained home-care providers, etc.

Housing 104 of intensive-care calculator 102 is preferably adapted to be hand-held during use (at least embodying herein hand-holdable housing means for housing such computer system) and comprises a physical size small enough to fit in the pocket of scrubs or a lab coat, as shown. Preferably, housing 104 comprises a "flip-open" design, as shown, comprising display screen portion 130 and keypad portion 132, as shown. Preferably, keypad portion 132 (at least embodying herein at least one first computer interface) and display screen portion 130 (at least embodying herein at least one second computer interface) are pivotally coupled by hinge element 134, as shown (at least embodying herein wherein such at least one hand-holdable housing comprises at least one hinge; and such at least one hinge is situate between such at least one first computer interface and such at least one second computer interface). Upon reading the teachings of this specification, those of ordinary skill in the art will now understand that, under appropriate circumstances, considering such issues as intended use, clinical environment, etc., other size and format arrangements, such as, for example, larger housings, incorporation of the system into other devices comprising alternate functions, etc., may suffice.

Figure 10:
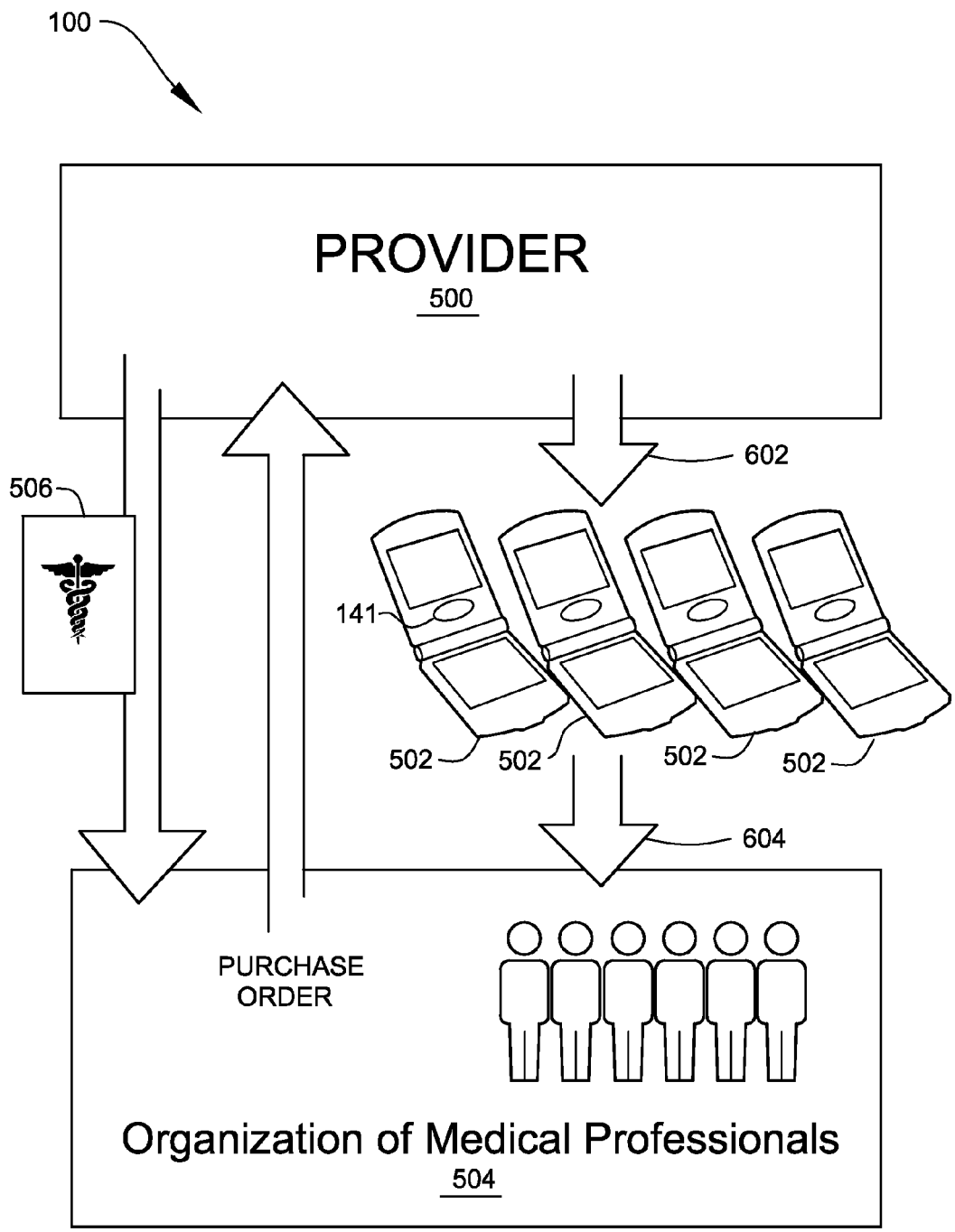
FIG. 10 shows a diagram illustrating a business method, related to use-promotion and accurate administration of at least one emergency medical drug, according to a preferred embodiment of the present invention.

Intensive-care calculator 102 is shown preferably comprising logo indicia 141, as shown. Logo indicia 141 can be applied by a supplier as part of a preferred business method wherein intensive-care calculator 102 is supplied to the user as a marketing incentive for a drug, medical product, or other medical-related service. In this way, intensive-care calculator 102 preferably functions as a promotional tool in conducting commerce within the medical field, as illustrated in FIG. 10. Upon reading the teachings of this specification, those of ordinary skill in the art will now understand that, under appropriate circumstances, considering such issues as intended use, clinical environment, etc., other business arrangements, such as, for example, use of an intensive-care calculator within the clinical environment to provide additional business benefits in the form of reduced insurance costs related to medical liability, a medical organization, such as a hospital, receiving a reduced coverage rate by implementing the use of intensive-care calculators within their standard medical procedures and protocols, etc., may suffice.

Preferably, intensive-care calculator 102 assists the user through calculation(s) by generating a sequence of prompts appearing on display 114 (at least embodying herein second computer interface means for displaying the at least one medical drug-administration-related drug-parameter output). Preferably, user input is provided at keypad 112, as best illustrated in FIG. 3 (at least embodying herein first computer interface means for assisting user input of the at least one medical drug-administration-related input). Preferably, both display 114 and keypad 112 are illuminated (in manners as known for other hand-held-type devices) to assist the user in viewing.

Preferably, keypad 112 and display 114 are operationally coupled to an internal electronic processor 116 (indicated by the dashed line depiction). Preferably, keypad 112 supplies user inputs to electronic processor 116. Preferably, electronic processor 116 (at least embodying herein computer processor means for generating the at least one medical drug-administration-related drug-parameter output) provides outputs that are visually readable at display 114, as shown.

Preferably, display 114 and electronic processor 116 each receive power from an internal power supply 118 (indicated by the dashed line depiction of FIG. 1), as shown. Intensive-care calculator 102 preferably comprises low battery warning visual indicator 115, to alert the user if the voltage drops below a predetermined value. Intensive-care calculator 102 further comprises an automatic power-saving feature that electrically decouples the power supply 118 after a predetermined period of inactivity (at least embodying herein at least one automatic power reducer adapted to automatically reduce the draw of the electrical power from such at least one power supply after at least one predetermined period without such user input at such at least one first computer interface). Preferably, electronic processor 116 is further coupled to audible warning element 124, preferably comprising a "speaker", designed to audibly alert a user that a predetermined parameter has been exceeded.

Figure 9:
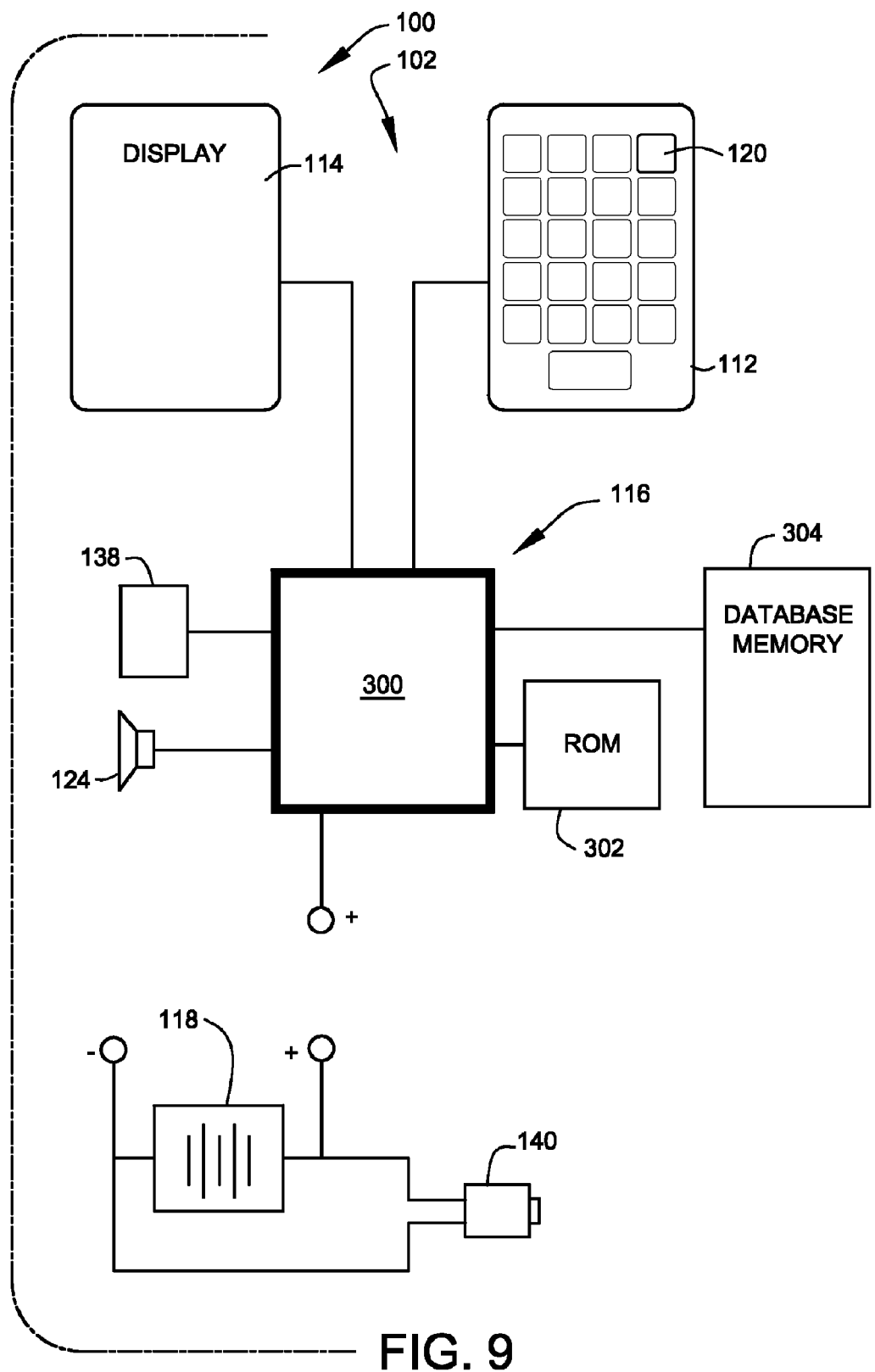
FIG. 9 shows a simplified block diagram, illustrating the general electronic organization of the intensive-care calculator, according to the preferred embodiment of FIG. 1.

Preferably, housing 104 comprises additional functional features such as belt clip 136 (see FIG. 2), external communication port 138, and external power connector 140, as further described in FIG. 9.

Figure 5:
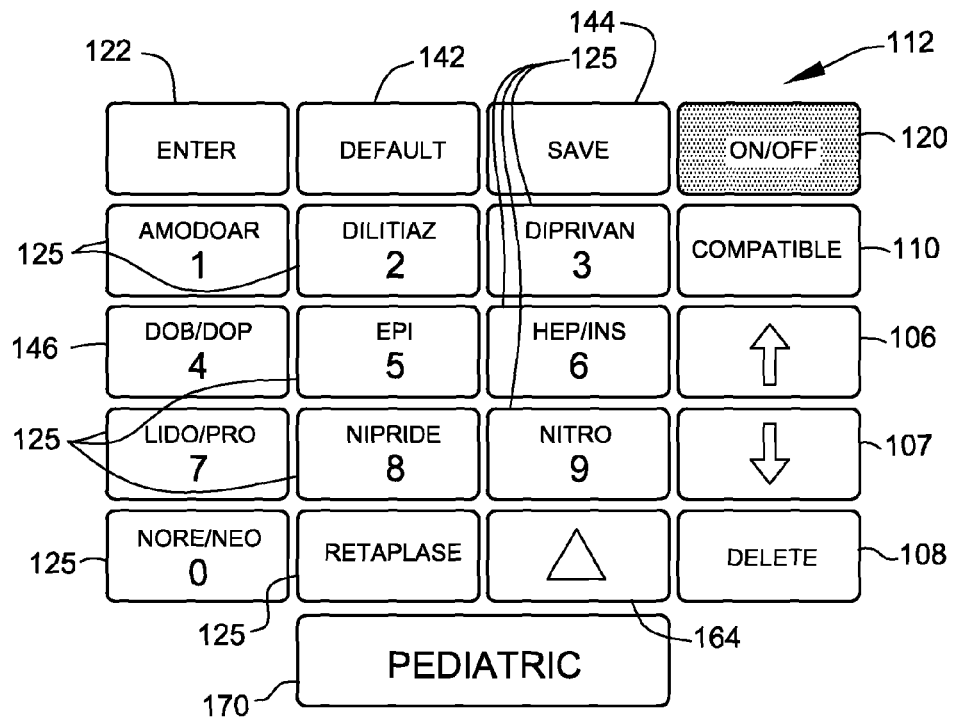
FIG. 5 shows a front view of a keypad of the intensive-care calculator, according to the preferred embodiment of FIG. 1.

FIG. 4 shows a front view of screen display 114 of intensive-care calculator 102 according to the preferred embodiment of FIG. 1. FIG. 5 shows a front view of keypad 112 of intensive-care calculator 102, according to the preferred embodiment of FIG. 1. Display 114 of FIG. 4 preferably comprises at least one electronic display screen, most preferably comprising a liquid crystal display (LCD) identified herein as display 114, as shown.

Preferably, display 114 is capable of rendering multiple lines of text and graphics, as shown. Preferably, display 114 is divided into multiple display areas, as shown. Preferably, upper display line 150 provides an indication, preferably, of adult or pediatric mode status. Preferably, text information within upper display line 150 is continuously displayed as a reminder to the user of Adult/Pediatric mode status. Preferably, lower display line 158 is reserved for the display of general system status information, such as, for example, text indicating the presence or number of saved drug entries, battery charge status, etc., as shown. Preferably, main display area 160 is used to display text and graphics directly relating to drug calculations and associated drug data, as shown.

Preferably, keypad 112 of FIG. 5 comprises an array of input keys supporting both general and specialized user inputs, as shown. Preferably, each input key comprises at least one visual marking (indicia) indicating its assigned function or functions, as shown. Preferably, the upper and right side input keys comprise general function keys, as shown. Below and to the left of the function keys resides a grouping of input keys providing direct input of commonly administered drugs, as shown.

A key feature of intensive-care calculator 102 is the ability of the user to directly select drugs from a plurality of dedicated drug input keys 125, located within keypad 112, as shown (at least embodying herein wherein such first computer interface means comprises actuator-button means for user-selecting a single one of such emergency medical drugs by a single user button actuation). Preferably, each dedicated drug input key 125 comprises indicia indicating at least one medical drug, preferably an emergency medical drug, to which it is assigned (at least embodying herein such at least one actuator-button comprises at least one first indicia indicating at least one such emergency medical drug). This highly preferred feature assists in quick and efficient execution of the medical calculations described herein. The preferred embodiment of the present invention may comprise dedicated drug input keys 125, for example, for the following drugs, as shown:

Amiodarone (AMODOAR)
Dilitiazem (DILITIAZ)
Diprivan (DIPRIVAN)
Dobutamine/Dopamine hydrochloride (DOB/DOP)
Ephinephrine (EPI)

Heparin/Insulin (HEP/INS)
Lidocaine/Procanamide (LIDO/PRO)
Sodium Nitropusside (NIPRIDE)
Nitroglycerine (NITRO)
Norepinephrine/Neosynephrine (NORE/NEO)
Retaplase Upon reading the teachings of this specification, those of ordinary skill in the art will now understand that, under appropriate circumstances, considering such issues as clinical environment, local protocols, specifics of medical field, etc., other dedicated key assignments, such as, for example, non-emergency oncology drugs, non-emergency pediatric drugs, non-emergency geriatric drugs, general non-emergency drugs, brand-name drugs, etc., may suffice.

In addition to dedicated drug assignments, dedicated drug input keys 125 preferably comprise numbers for numerical entries, as shown. Preferably, the number organization is in a telephone-style format that increases in value from top to bottom, as shown.

Preferably, medical drug management system 100 comprises at least one mode-changing capability wherein keypad 112 comprises at least one dedicated mode-selector button adapted to allow a user to select among at least two unique operational modes. This preferred mode-changing feature allows the user to adjust the mode of operation of intensive-care calculator 102 to a unique set of medical drug parameters. In the present disclosure, a medical drug parameter shall be defined to include, preferably, specific emergency medical drugs. In intensive-care calculator 102, the mode changing feature is embodied herein as "PEDIATRIC" key 170, as shown.

Preferably, "PEDIATRIC" key 170 may function to change all calculations and related pediatric emergency drug data to conform to pediatric parameters (at least embodying herein wherein such first computer interface means further comprises actuator-button mode means for selecting among at least two actuator-button modes wherein each such actuator-button mode provides actuator-button access for user-selecting among a unique set of such medical drug parameters). Pressing "PEDIATRIC" key 170 preferably toggles the text of upper display line 150 to provide a clear indication, for example, of adult or pediatric mode status. Preferably, if the drug indicated on keypad 112 is not recommended for this mode change, the drug parameters will not change. Upon reading the teachings of this specification, those of ordinary skill in the art will now understand that, under appropriate circumstances, considering such issues as intended use, nature of medical field, etc., other mode change arrangements, such as, for example, changing modes to adjust between medical conditions, changing modes to adjust between approved protocols (such as emergency, non-emergency, pediatric, adult, oncology, etc.), changing modes to adjust between physician preferences, changing modes to adjust between medical facility preferences/protocols, changing modes to adjust between languages, changing modes to adjust between units of measure, etc., may suffice.

Preferably, the indicia notation of keypad 112 is adjustable to match changes in mode. For example, keypad 112 may comprise an attachable overlay, having mode-specific indicia. In alternate preferred embodiments, the marking indicia may automatically change with the mode by electronic means. For example, one or more keys of keypad 112 may preferably comprise a liquid crystal display controlled by electronic processor 116 to produce a display as shown in FIG. 5 using known electronic methods/parts. Thus, the displayed indicia is preferably updated in concert with change in operational mode (at least embodying herein wherein such at least one actuator-button comprises at least one first indicia indicating at least one such emergency medical drug, and wherein each such at least two actuator-button modes comprise at least one set of such first indicia; and such mode changes comprise variation in such first indicia of such at least one actuator-button). Electronic display switches of this general type are produced under the "Smartswitch" trade name as produced by NNK Corporation of Scottsdale, Ariz. Upon reading the teachings of this specification, those of ordinary skill in the art will now understand that, under appropriate circumstances, considering such issues as intended use, advances in technology, etc., other keypad arrangements, such as, for example, touch screen displays, etc., may suffice.

Referring again to keys of keypad 112, in most calculations pressing "ENTER" key 122 preferably accepts the user's input for a selected drug, drug parameter, or numerical value. Preferably, pressing "UP" arrow key 106 and "DOWN" arrow key 107 functions to scroll main display area 160 or to move through user entries and selections. Pressing "DELETE" key 108 preferably restarts an entry. Once an infusion rate is calculated, the "DELETE" key 108 is preferably used to start a new calculation.

Preferably, "SAVE" key 144 allows the user to save multiple drug entries for later recall and use. Preferably, the user can perform a calculation, press "SAVE" key 144, and initiate a new entry by pressing a new drug key, without losing the previous drug entry and associated data. Preferably, saved drug entries remain stored in system memory, preferably categorized by drug name, until deleted by the user, as described below. In addition, intensive-care calculator 102 can preferably power off without losing the stored drug entries, as further described in FIG. 9.

When intensive-care calculator 102 is again powered on, the user preferably presses "SAVE" key 144 on keypad 112 to generate a list of saved drug entries. Preferably, the first saved drug entry will be visually highlighted on display 114. If the user wishes to recall the highlighted entry, the user presses "ENTER" key 122 and the associated display screen will be recalled from memory and displayed. If the highlighted item is not the drug entry of interest, the user preferably uses "UP" arrow key 106 and "DOWN" arrow key 107 to scroll through the list until the desired drug entry is highlighted. Preferably, pressing "ENTER" key 122 recalls the highlighted selection that is returned from memory and displayed on display 114.

To delete a drug entry the user will preferably scroll to the highlighted entry press "DELETE" key 108 followed by "ENTER" key 122. The drug entry is then permanently removed from memory.

Figure 6:
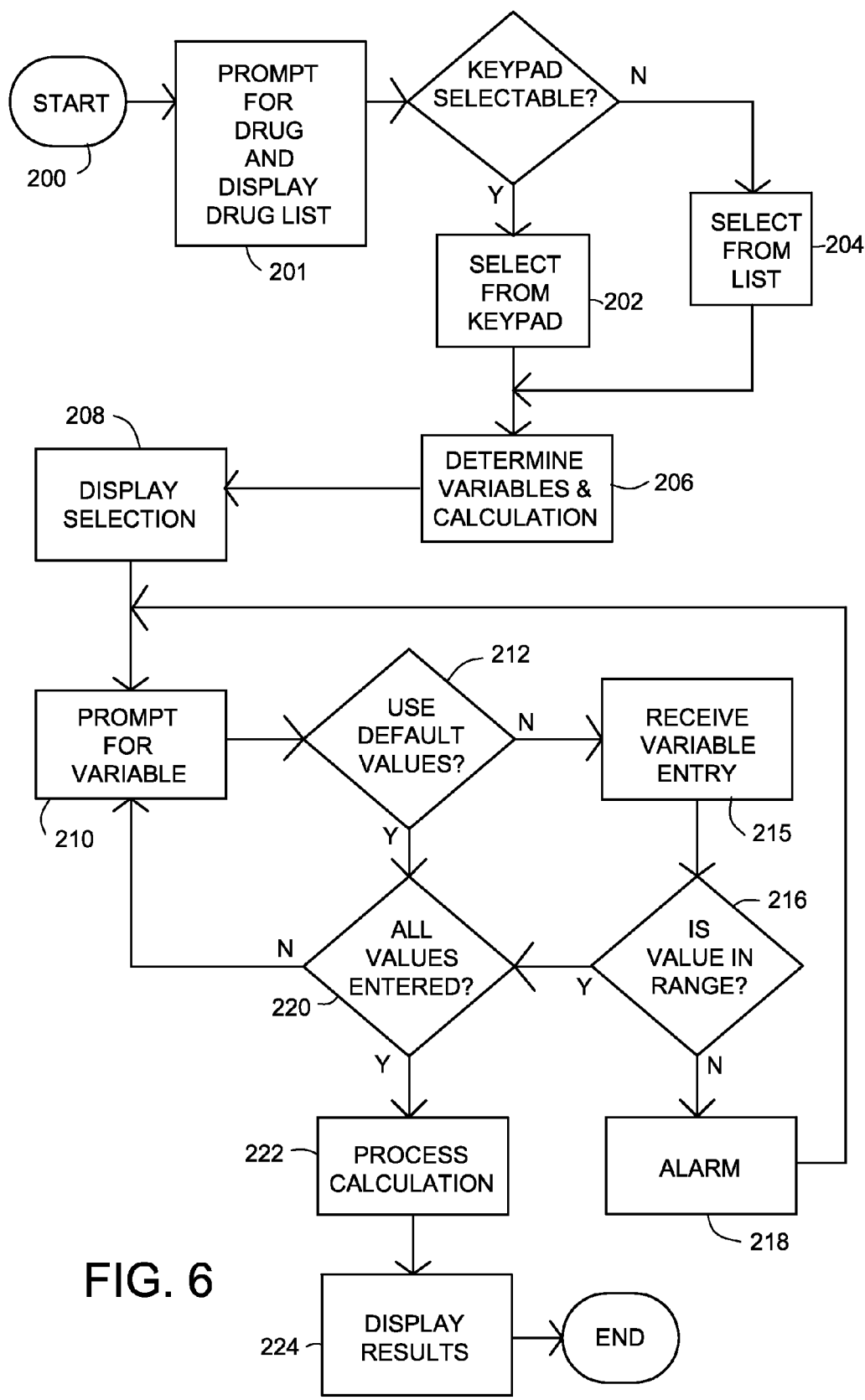
FIG. 6 shows a flowchart diagram illustrating the general operation of the intensive-care calculator, according to a preferred embodiment of the present invention.

FIG. 6 shows a diagram illustrating the general operation of intensive-care calculator 102 according to a preferred embodiment of the present invention. Referring to FIG. 6 with continued reference to FIG. 1 through FIG. 5, operation of intensive-care calculator 102 is preferably initiated by pressing on/off switch 120 to commence the operation of electronic processor 116 and display 114, as represented in step 200. Initially, electronic processor 116 is preferably adapted to generate within display 114 an indication of adult or pediatric mode status at line 150 and a user drug selection prompt at main display area 160. Preferably, display 114 prompts the user for a drug selection by displaying the text "Drug:_" at the beginning of line 152, as shown in FIG. 4, along with the display of a drop down list of drugs as represented by step 201. If the drug to be selected comprises a commonly utilized intravenous drug, the user has the preferred option of performing a direct selection of the drug from the appropriate dedicated drug input key 125 of keypad 112 and confirming the selection by pressing "ENTER" key 122, as represented in step 202. If the drug does not appear on keypad 112, the user preferably selects the appropriate drug from display 114 by scrolling through a stored drug list and by pressing "ENTER" key 122 once the appropriate drug is highlighted, as represented in alternate step 204. Under either selection method, electronic processor 116 functions to select the appropriate formula and applicable alarm parameters, as represented in step 206, and the drug selection is visually confirmed by its display on line 152 of display 114 as represented in step 208. It should be noted that, after the drug has been selected, the user has the preferred option of viewing a list of compatible drugs at any time by pressing "COMPATIBILITY" key 110 (at least embodying herein drug compatibility means for determining compatibility of at least one first such at least one emergency medical drug with at least one second such at least one emergency medical drug).

Completing the selection of the appropriate drug preferably initiates a series of prompts requesting user entry for the numerical parameters appropriate to the specific drug selected by the user, as represented in step 210. For example, if the drug Dopamine is the drug selected by the user, intensive-care calculator 102 generates a displayed user prompt requesting the user to input the appropriate drug amount along with a displayed list of selectable default drug amounts.

Preferably, the user selects the appropriate drug amount from display 114 by scrolling through the displayed default list and by pressing "ENTER" key 122 once the appropriate value is highlighted. The user also has the option of completing the input of multiple variables using the "DEFAULT" key 142, as represented in step 212, described in further detail below.

Preferably, the drug amount is visually confirmed by its display on line 152 of display 114. If the appropriate drug amount does not appear on the displayed default list, the user preferably inputs the drug amount by manually pressing the appropriate number keys of keypad 112 followed by "ENTER" key 122. Preferably, electronic processor 116 checks the entry against appropriate values stored in a memory database of the device, as represented in step 216. If the user manually inputs a drug amount that exceeds the normal parameters, either higher or lower than recommended, the display 114 will flash, audible warning element 124 will sound, and electronic processor 116 will not proceed with the calculation until an acceptable input is received from the user, as represented in step 218. If the manually entered drug amount is within standard parameters, electronic processor 116 accepts the input and displays the selected drug amount on line 152 of display 114.

Preferably, electronic processor 116 then proceeds to the next parameter question (repeating step 210), which, in the example of Dopamine, comprises a selection of fluid volume. In the drug calculation, the preprogrammed sequence of prompts and checks will preferably repeat until electronic processor 116 has confirmed that all necessary variables have be entered, as represented in step 220.

Continuing the example calculation for the drug Dopamine, the user is next prompted to input a fluid volume by screen display of the text "VOLUME_" at the beginning of line 154 of display 114, along with a displayed list of selectable default fluid volumes. Note that in the screen display depiction of FIG. 4, default volume values (250 cc and 500 cc) are displayed at line positions 154a and 154b. Also, note that the upper volume value of 250 cc, at line positions 154a, is visually highlighted for selection. Preferably, the user selects the appropriate fluid volume from display 114 by scrolling through the displayed list of default values and by pressing "ENTER" key 122 once the appropriate volume is highlighted. Preferably, the selected fluid volume is visually confirmed by its display on line 154 of display 114. If the appropriate fluid volume does not appear on the displayed default list, the user preferably inputs the fluid volume by manually pressing the appropriate number keys of keypad 112, followed by "ENTER" key 122. Preferably, electronic processor 116 then proceeds to the next parameter question, which, in the example of Dopamine, comprises a selection of drug dosage.

Preferably, again repeating step 210 of the sequence, the user is prompted to input a prescribed dosage (per the physician's order) by displaying the text "DOSE_" at the beginning of line 156 of display 114. Preferably, the user inputs the prescribed dose by manually pressing the appropriate number keys of keypad 112, followed by "ENTER" key 122, as indicated in step 215. Again, electronic processor 116 preferably confirms if the user has manually inputted a dosage that exceeds the normal parameters (as stored in the database), either higher or lower than recommended. If this condition has occurred, electronic processor 116 will generate a signal adapted to trigger the display 114 to flash and audible warning element 124 to sound (at least embodying herein alarm means for generating at least one alarm signal discernable by the at least one medical professional; wherein such computer storage means comprises computer database means for providing predetermined acceptable user input ranges for the at least one medical drug-administration-related input; wherein such computer processor means comprises activator means for activating such alarm means; and wherein such activator means activates such alarm means when the at least one medical drug-administration-related input deviates from the predetermined acceptable user input ranges for the at least one medical drug-administration-related input). Preferably, electronic processor 116 will return the sequence to step 210 and repeat the prompt, excepting a new variable entry, as indicated in step 215. This preferred sequence will continue until an acceptable input is received from the user.

If the manually entered dosage is within standard parameters, electronic processor 116 accepts the input and displays the dosage on line 156 of display 114. Upon reading the teachings of this specification, those of ordinary skill in the art will now understand that, under appropriate circumstances, considering such issues as intended use, cost, clinical environment, etc., other user-assisting display arrangements, such as, for example, displaying the efficacious high and low parameters for normal dosage range during user entry, etc., may suffice.

Preferably, in the next preferred step, the user is prompted to input the patient's weight by displaying the text "WT_" at the beginning of line 162 of display 114. Preferably, the user inputs the prescribed dose, again by manually pressing the appropriate number keys of keypad 112, followed by pressing "ENTER" key 122. Again, if the user manually inputs a patient weight that falls outside the expected range for human weight, the display 114 will flash, audible warning element 124 will sound, and electronic processor 116 will not proceed with the calculation until an acceptable input is received from the user. Preferably, if the manually-entered patient weight is within expected parameters, electronic processor 116 confirms that all required variables have been entered (step 220) then calculates the correct infusion rate, as indicated in step 222. Preferably, the results of the calculation are displayed at line 166 of display 114, as indicated in step 224, along with a scrollable list of incompatible drugs. The user may preferably save the calculation for future recall by pressing "SAVE" key 144, or may start a new calculation by pressing "DELETE" key 108.

The above-described example calculation is representative of only one calculation for a specific drug. Intensive-care calculator 102 preferably comprises a stored database of many drugs, each comprising specific calculation parameters. Upon reading the teachings of this specification, those of ordinary skill in the art will now understand that, under appropriate circumstances, considering such issues as intended use, cost, complexity of design, etc., other calculation and input arrangements, such as, for example, allowing the user to solve any of the variable fields by supplying a combination of known variables, etc., may suffice.

Reference is again made to FIG. 5 and the preferred key arrangements of keypad 112. Preferably, intensive-care calculator 102 comprises a number of additional features adapted to improve the speed and accuracy of the various medical calculations described herein.

"DEFAULT" key 142 preferably expedites user calculation by providing a "one-touch" entry of multiple default values. More specifically, "DEFAULT" key 142 allows the user to automatically input multiple preset values for clinically prevalent drug amounts, concentrations, volumes, etc. This greatly increases the rate at which the calculation parameters are entered by reducing the number of required user inputs.

Figure 7:
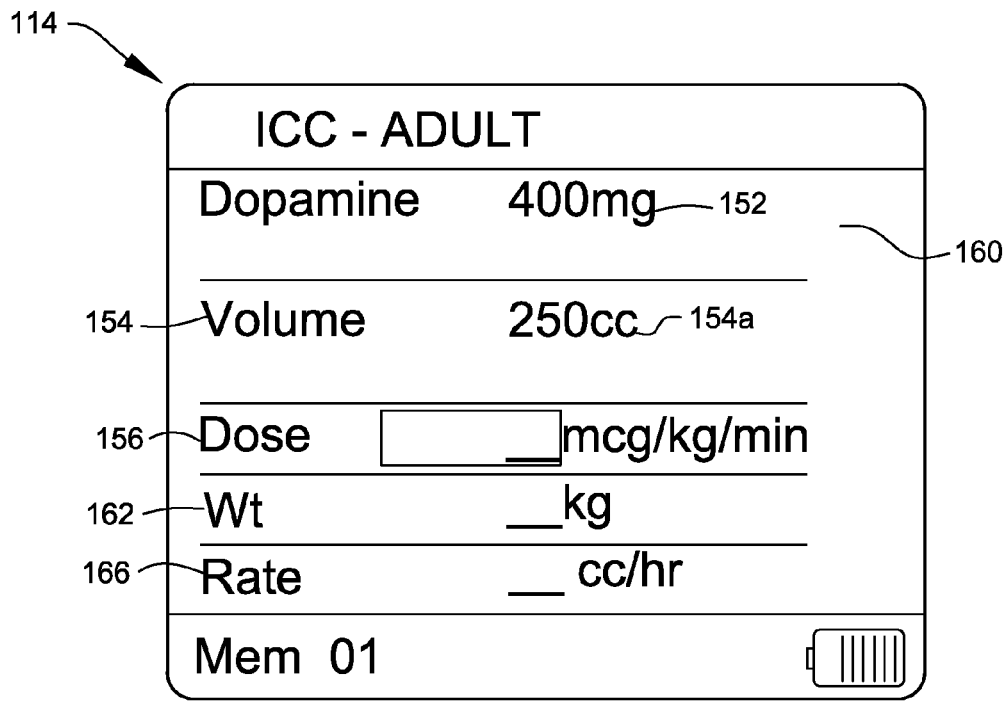
FIG. 7 shows a screen display depicting instant entry of default data values using a default entry key, according to the preferred embodiment of FIG. 1.

The example screen display of FIG. 7 illustrates the advantages of using "DEFAULT" key 142 in the example drip-rate calculation for the drug Dopamine. As previously described, the user is preferably prompted for a drug selection by displaying the text "Drug:_" at the beginning of line 152, as shown. In response to the prompt, the user selects the drug Dopamine, directly from keypad 112, by pressing "DOB/DOP" key 146 followed by "ENTER" key 122. On completing the selection, the text "Dopamine" is added to line 152, as shown. The user is then prompted to enter the drug amount on line 152, followed by a prompt for fluid volume at line 154. If the medical professional is utilizing commonly applied materials comprising standard volumes and amounts, the user presses "DEFAULT" key 142 followed by "ENTER" key 122. Intensive-care calculator 102 preferably completes the entries on behalf of the user by entering a default value of 400 mg for "Drug: Dopamine", at line 152, and a default value of 250 cc for "Volume:_" at line 154, as shown.

Preferably, intensive-care calculator 102 immediately drops to the next user prompt by highlighting the input for Dosage at line 158, as shown. The user then completes the calculation for drip rate by entering the prescribed dose followed by the patient's weight. Thus, "DEFAULT" key 142 preferably allows the user to enter weight and dose only by immediately selecting normal drug amounts and volumes without hitting the individual keys for entry. It is noted that the combining of the dedicated-keys systems and the default systems of the preferred embodiment of the present invention provides needed decision speeds, especially in critical care and emergencies. "DEFAULT" key 142 at least embodies herein wherein such second computer interface means comprises default-display means for displaying at least one situational-default set of the at least one medical drug-administration-related drug-parameter output; and at least embodies herein wherein such first computer interface means comprises at least one dedicated "default-type" key to input at least one request to display such at least one situational-default set of the at least one medical drug-administration-related drug-parameter output.

Figure 8:
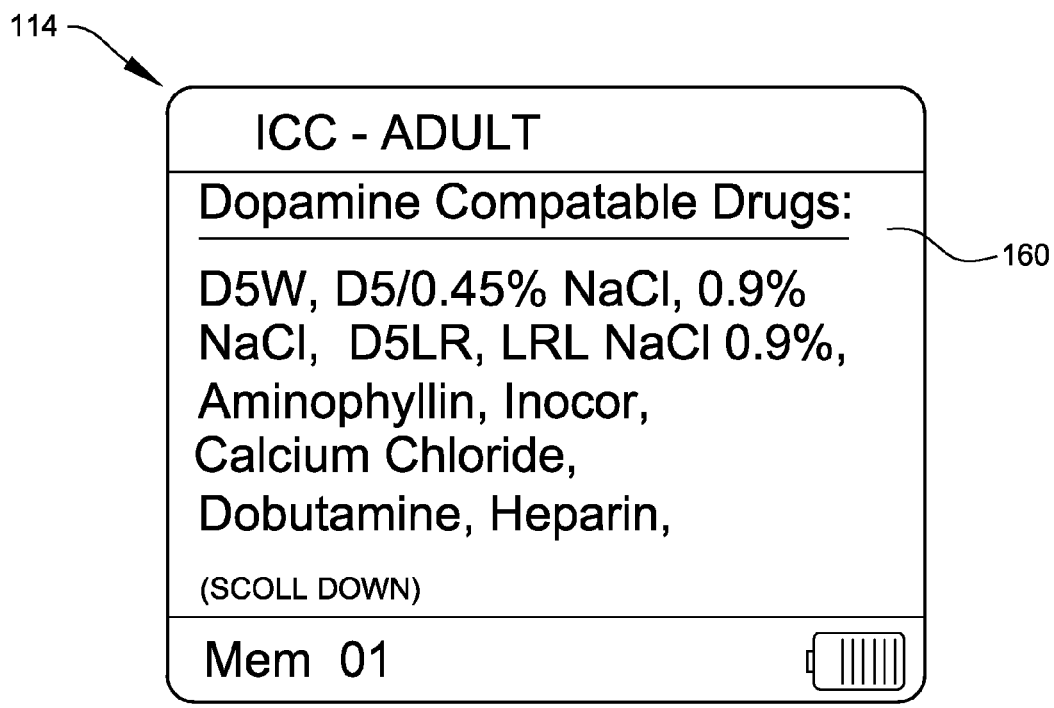
FIG. 8 shows a screen display, depicting the listing of drug compatibility data, according to the preferred embodiment of FIG. 1.

Preferably, at any time after the drug has been selected, the user has the option of viewing a list of compatible drugs by pressing "COMPATIBILITY" key 110. Pressing "COMPATIBILITY" key 110 preferably provides compatible and incompatible drug information as well as intravenous fluid data. Pressing "COMPATIBILITY" key 110, after a drug selection has been entered, will preferably generate and display a list of compatible and incompatible drugs, as best illustrated in FIG. 8.

Additionally, "COMPATIBILITY" key 110 preferably functions to allow the user to confirm the compatibility of two or more drugs to be infused along a single common line (at least embodying herein drug compatibility means for determining compatibility of at least one first such at least one emergency medical drug with at least one second such at least one emergency medical drug). For example, "COMPATIBILITY" key 110 is preferably adapted to allow the user to first select the primary drug (the drug selectable from the keypad 112 that is currently infusing) and then press "COMPATIBILITY" key 110 followed by a second drug the user wishes, for example, to infuse in the same line, also preferably selectable from keypad 112. Preferably, display 114 will show both drugs and state compatibility. If the second drug is not on keypad 112, the user presses "COMPATIBILITY" key 110 twice and scrolls through a displayed list of drugs. Preferably, the drugs displayed will be organized in alphabetical order by generic name. The user will preferably see the first drug highlighted and use scroll key to read the selection. On completing review of the list, the user preferably presses "ENTER" key 122 to return to the previous screen.

Preferably, Delta/Titration key 164 is used to change parameters of a saved drug entry. Preferably, to use Delta/Titration key 164, the user presses "SAVE" key 144 to recall a list of saved entries. Preferably, pressing "UP" arrow key 106 or "DOWN" arrow key 107 allows the user to scroll through the displayed list until the target drug entries highlighted. Preferably, the user recalls the entry to be edited by pressing Delta/Titration key 164 followed by "ENTER" key 122. Preferably, the drug entry is recalled from memory with the previously entered drug variables (concentration, volume, weight and dose, etc.) appearing on display 114. The user preferably chooses the variable to be changed by pressing "UP" arrow key 106 or "DOWN" arrow key 107 until the target variable is highlighted. The user then preferably updates the target variable and presses "ENTER" key 122 wherein the drug entry is recalculated (at least embodying herein wherein such at least one computer processor comprises at least one editor adapted to assist at least one user edit to at least one of the least one medical drug-administration-related inputs stored within such at least one drug-entry storage) with the new result (for example, drip rate) appearing on display 114. The user preferably presses "SAVE" key 144 to save the new calculation.

FIG. 9 and shows a simplified block diagram illustrating the general electronic organization of intensive-care calculator 102. It will be understood that the operational sequence described above is accomplished by programming electronic processor 116 in accordance with programming principles that are well known in the art.

Preferably, electronic processor 116 comprises an assembly of interoperable components of a digital or mixed signal semiconductor design. Electronic processor 116 preferably comprises at least one internal logic processor 300 that may comprise well-known logic structures such as registers for arithmetic operation, address control registers, stack pointers, instruction registers, instruction decoders, etc. Preferably, internal logic processor 300 is electrically coupled with peripheral circuits by means of internal address and data buses. Preferably, electronic processor 116 further comprises factory-installed software programming adapted to operate logic processor 300. Preferably, electronic processor 116 is operationally coupled to display 114 and keypad 112 as shown.

Electronic processor 116 further preferably comprises at least one read-only memory (ROM) 302 that preferably contains the operating system instructions for logic processor 300, as shown. Upon reading the teachings of this specification, those of ordinary skill in the art will now understand that, under appropriate circumstances, considering such issues as intended use, system design, etc., other ROM memory content, such as, for example, a drug database, a user-stored drug calculation, etc., may suffice.

Electronic processor 116 further preferably comprises at least one mass storage memory 304 that preferably contains a database of drug parameters, calculations, user-stored drug entries and completed calculations, etc. Memory 304 at least embodies herein computer storage means for storing at least one drug database comprising a plurality of known medical drug parameters, and it further embodies herein wherein such at least one computer storage comprises at least one drug-entry storage adapted to store the at least one medical drug-administration-related input and the at least one drug parameter output. Preferably, data contained within mass storage memory 304 remains resident when intensive-care calculator 102 is powered off. This preferred feature is enabled by the implementation of at least one nonvolatile memory device, which preferably includes such technology as Electrically-Erasable Programmable Read-Only Memory (EEPROM) modules and/or similar FLASH-based variants, battery backup circuits, nonvolatile random access memory (RAM) chips, etc.

Because mass storage memory 304 is preferably coupled to external communication port 138 through logic processor 300, the connection of intensive-care calculator 102 to at least one compatible external electronic data source, such as a computer, allows periodic updates of the database within mass storage memory 304. Preferably, electronic processor 116, on detection of a communication connection of external communication port 138 to a compatible computer, begins a "download/setup" routine that includes the prompting of download acceptance, display of status, etc., on display 114, thus alerting the user that a download routine is occurring. It is also within the scope of the present invention to provide, under appropriate circumstances, preferred embodiments comprising at least one wireless data link, utilizing, as one example, an infrared data receiver. Upon reading the teachings of this specification, those of ordinary skill in the art will now understand that, under appropriate circumstances, considering such issues as intended use, design preference, advances in technology, etc., other database update arrangements, such as, for example, removable data cards, removable data media, wireless connectivity to external databases, etc., may suffice. Furthermore, upon reading the teachings of this specification, those of ordinary skill in the art will now understand that, under appropriate circumstances, considering such issues as intended use, etc., other update arrangements, such as, for example, displaying periodic reminders to update data, providing periodic reminders of website URLs, etc., may suffice.

Electronic processor 116 preferably comprises at least one internal power supply 118 preferably supplying power to logic processor 300 and the other power dependant components of intensive-care calculator 102, as shown. Preferably, internal power supply 118 comprises one or more replaceable batteries located within keypad portion 132 (shown in FIG. 1). Preferably, internal power supply 118 comprises external power connector 140 allowing an A/C-type power adapter to supply power directly to intensive-care calculator 102, by bypassing battery power supplied from internal power supply 118. It is within the scope of the present invention to provide an embodiment of internal power supply 118 comprising an arrangement of one or more rechargeable batteries that are periodically renewed by the connection to the external power source. Preferably, the circuit of internal power supply 118 can be turned off by electronic processor 116 on detection of a momentary closed condition at power on/off switch 120, or after intensive-care calculator 102 has been idle for 1½ minutes with no activity.

Audible warning element 124 is preferably triggered by a signal generated at an output pin of electronic processor 116. An intermediate controlling device, such as a switching transistor may preferably be used, if the output level of electronic processor 116 and the current draw of audible warning element 124 are not matched.

FIG. 10 shows a diagram illustrating a method related to use-promotion and accurate administration of at least one drug, preferably at least one emergency medical drug, using medical drug management system 100, according to a preferred embodiment of the present invention. Intensive-care calculator 102 is shown in FIG. 1 preferably comprising logo indicia 141. Additional drug-specific indicia can be applied to intensive-care calculator 102 as part of a preferred method wherein intensive-care calculator 102 is supplied to a medical professional as a marketing incentive promoting a drug, medical product, or other medical-related service.

Preferably, at least one provider 500 produces hand-held computer devices 502 (an intensive-care calculator embodiment such as intensive-care calculator 102) having actuator-buttons dedicated to a set of medical drugs 506 selected by provider 500, as indicated in step 602. Preferably, medical drug 506 comprises at least one emergency or critical care drug. Upon reading the teachings of this specification, those of ordinary skill in the art will now understand that, under appropriate circumstances, considering such issues as intended use, medical field, etc., other drug types, such as, for example, non-emergency drugs, etc., may suffice. Preferably, each hand-held computer device 502 comprises actuator-buttons bearing indicia specifically relating to emergency medical drugs 506, for example a brand-name or patented drug.

Preferably, provider 500 provides hand-held computer devices 502 to at least one organization of medical professionals 504, as illustrated in step 604. In the present example, the organization of medical professionals 504 preferably comprises a hospital, healthcare network, or medical practice purchasing quantities of medical drugs, including emergency medical drugs (in the course of performing medical services), as shown. Upon reading the teachings of this specification, those of ordinary skill in the art will now understand that, under appropriate circumstances, considering such issues as market structure, distribution chain, etc., other arrangements, such as, for example, providing the hand-held computer devices to an intermediate distributor, directly to nurse or paramedic, etc., may suffice.

Preferably, such distribution assists use-promotion of hand-held computer devices 502 by the organization of medical professionals 504; wherein use of such set of medical drugs 506 is promoted. For example, provider 500 may contact the drug purchasing entity for the organization of medical professionals 504 and offer to underwrite the cost of hand-held computer devices 502, in consideration of the purchase of medical drugs 506. The purchase incentive to the organization of medical professionals 504 is in the potential for improved patient care, improved staff motivation, and reduced medical liability. Once the units are distributed, they continue to offer promotion opportunities to provider 500 by means of periodic database updates of newly offered drug products. Furthermore, download data can provide additional means for improving future product sales.

Preferably, provider 500 comprises at least one drug purveyor, preferably an emergency drug purveyor. Preferably, the set of emergency medical drugs 506 comprise drugs developed, produced, offered, or promoted by provider 500.

Although applicant has described applicant's preferred embodiments of this invention, it will be understood that the broadest scope of this invention includes modifications such as diverse shapes, sizes, and materials. Such scope is limited only by the below claims as read in connection with the above specification. Further, many other advantages of applicant's invention will be apparent to those skilled in the art from the above descriptions and the below claims.

What is claimed is:

1. A computer system related to electronically assisting at least one medical professional to accurately generate at least one drug parameter output, relating to the administration of at least one emergency medical drug, a resultant of at least one medical calculation utilizing at least one medical drug administration-related input by the at least one medical professional, said system comprising:
    a) hand-holdable housing means for housing said computer system;
    b) computer storage means for storing at least one drug database comprising a plurality of known medical drug parameters;
    c) first computer interface means for assisting user input of the at least one medical drug-administration-related input;
    d) second computer interface means for displaying the at least one medical drug-administration-related drug-parameter output;
    e) computer processor means for generating the at least one medical drug-administration-related drug-parameter output; and
    f) power supply means for supplying electrical power to assist operation of said computer system;
    g) wherein said first computer interface means comprises actuator-button means for user-selecting a single one of such emergency medical drugs by a single user button actuation; and
    h) wherein said first computer interface means further comprises actuator-button mode means for selecting among at least two actuator-button modes wherein each such actuator-button mode provides actuator-button access for user-selecting among a unique set of known emergency medical drug parameters.

2. The computer system according to claim 1 further comprising:
    a) alarm means for generating at least one alarm signal discernable by the at least one medical professional;
    b) wherein said computer storage means comprises computer database means for providing predetermined acceptable user input ranges for the at least one medical drug-administration-related input;
    c) wherein said computer processor means comprises activator means for activating said alarm means; and
    d) wherein said activator means activates said alarm means when the at least one medical drug-administration-related input deviates from the predetermined acceptable user input ranges for the at least one medical drug-administration-related input.

3. The computer system according to claim 1 further comprising drug compatibility means for determining compatibility of at least one first such at least one emergency medical drug with at least one second such at least one emergency medical drug.

4. A computer system related to electronically assisting at least one medical professional to accurately generate at least one drug parameter output, relating to the administration of at least one emergency medical drug, a resultant of at least one medical calculation utilizing at least one medical drug-administration-related input by the at least one medical professional, said system comprising:
    a) at least one hand-holdable housing adapted to house said computer system;
    b) at least one computer storage adapted to store at least one drug database comprising a plurality of known medical drug parameters;
    c) at least one first computer interface adapted to assist user input of the at least one medical drug-administration-related input;
    d) at least one second computer interface adapted to display the at least one medical drug-administration-related drug-parameter output; and
    e) at least one computer processor adapted to generate the at least one medical drug-administration-related drug-parameter output; and
    f) at least one power supply adapted to supply electrical power to assist operation of said computer system;
    g) wherein said at least one first computer interface comprises at least one actuator-button adapted to user-select a single one of such emergency medical drugs by a single user button actuation; and
    h) wherein said at least one first computer interface further comprises at least one actuator-button mode selector adapted to select among at least two actuator-button modes wherein each such actuator-button mode provides actuator-button access for user-selecting among a unique set of known medical drug parameters.

5. The computer system according to claim 4 further comprising:
    a) at least one alarm adapted to generate at least one alarm signal discernable by the at least one medical professional;
    b) wherein said at least one computer storage comprises at least one computer database adapted to provide predetermined acceptable user input ranges for the at least one medical drug-administration-related input;
    c) wherein said at least one computer processor comprises at least one activator signal adapted to activate said at least one alarm; and
    d) wherein said at least one activator signal is adapted to activate said at least one alarm when the at least one medical drug-administration-related input deviates from the predetermined acceptable user input ranges for the at least one medical drug-administration-related input.

6. The computer system according to claim 4 further comprising at least one drug compatibility determiner for computer-determining compatibility of at least one first such at least one emergency medical drug with at least one second such at least one emergency medical drug.

7. The computer system according to claim 4 wherein:
    a) said at least one hand-holdable housing comprises at least one hinge; and
    b) said at least one hinge is situate between said at least one first computer interface and said at least one second computer interface.

8. The computer system according to claim 4 wherein said at least one actuator-button comprises at least one first indicia indicating at least one such emergency medical drug.

9. The computer system according to claim 8 wherein:
   a) each said at least two actuator-button modes comprise at least one set of said first indicia; and
   b) such mode changes comprise variation in such first indicia of said at least one actuator-button.

10. The computer system according to claim 4 wherein said at least one computer storage comprises at least one drug-entry storage adapted to store the at least one medical drug-administration-related input and the at least one drug parameter output.

11. The computer system according to claim 10 wherein said at least one computer processor comprises at least one editor adapted to assist at least one user edit to at least one of the least one medical drug-administration-related inputs stored within said at least one drug-entry storage.

12. The computer system according to claim 4 further comprising at least one external data transfer port adapted to assist at least one transfer of data between at least one external data source and said at least one computer storage.

13. The computer system according to claim 4 wherein said at least one second computer interface comprises at least one display illuminator adapted to generate illumination assisting visual user interface.

14. The computer system according to claim 4 wherein said at least one actuator-button comprises at least one button illuminator adapted to generate illumination assisting user button interface.

15. The computer system according to claim 4 wherein:
   a) at least one of said at least two actuator-button modes comprises at least one adult mode; and
   b) at least one of said at least two actuator-button modes comprises at least one pediatric mode.

16. The computer system according to claim 4 further comprising at least one automatic power reducer adapted to automatically reduce the draw of the electrical power from said at least one power supply after at least one predetermined period without such user input at said at least one first computer interface.

17. The computer system according to claim 4 wherein such emergency medical drugs of said at least one actuator-button comprises at least one member selected from the group consisting essentially of:
   a) Amiodarone,
   b) Dilitiazem,
   c) Diprivan,
   d) Dobutamine,
   e) Dopamine Hydrochloride,
   f) Ephinephrine,
   g) Heparin,
   h) Insulin,
   i) Lidocaine,
   j) Procanamide,
   k) Sodium Nitropusside,
   l) Nitroglycerine,
   m) Norepinephrine,
   n) Neosynephrine,
   o) Retaplase, and
   p) Isoproterenol.

18. A computer system related to electronically assisting at least one medical professional to accurately generate at least one drug parameter output, relating to the intravenous administration of at least one medical drug, a resultant of at least one medical calculation utilizing at least one medical drug-administration-related input by the at least one medical professional, said system comprising:
   a) hand-holdable housing means for housing said computer system;
   b) computer storage means for storing at least one drug database comprising a plurality of known medical drug parameters;
   c) first computer interface means for assisting user input of the at least one medical drug-administration-related input;
   d) second computer interface means for displaying the at least one medical drug-administration-related drug-parameter output;
   e) computer processor means for generating the at least one medical drug-administration-related drug-parameter output; and
   f) power supply means for supplying electrical power to assist operation of said computer system;
   g) wherein said first computer interface means comprises actuator-button means for user-selecting a single one of such medical drugs by a single user button actuation; and
   h) wherein said first computer interface means further comprises actuator-button mode means for selecting among at least two actuator-button modes wherein each such actuator-button mode provides actuator-button access for user-selecting among a unique set of known medical drug parameters.

19. The computer system according to claim 18 wherein said second computer interface means comprises default-display means for displaying at least one situational-default set of the at least one medical drug-administration-related drug-parameter output.

20. The computer system according to claim 19 wherein said first computer interface means comprises at least one dedicated "default-type" key to input at least one request to display such at least one situational-default set of the at least one medical drug-administration-related drug-parameter output.

* * * * *